US009729966B2

(12) United States Patent
Pan

(10) Patent No.: US 9,729,966 B2
(45) Date of Patent: Aug. 8, 2017

(54) ACTIVE NOISE REDUCTION ENGINE SPEED DETERMINING

(71) Applicant: Bose Corporation, Framingham, MA (US)

(72) Inventor: Davis Y. Pan, Arlington, MA (US)

(73) Assignee: Bose Corporation, Framingham, MA (US)

( * ) Notice: Subject to any disclaimer, the term of this patent is extended or adjusted under 35 U.S.C. 154(b) by 147 days.

(21) Appl. No.: 14/812,560

(22) Filed: Jul. 29, 2015

(65) Prior Publication Data

US 2015/0334490 A1 Nov. 19, 2015

Related U.S. Application Data

(63) Continuation of application No. 11/426,512, filed on Jun. 26, 2006, now abandoned.

(51) Int. Cl.

| | |
|---|---|
| ***G10K 11/16*** | (2006.01) |
| ***A61F 11/00*** | (2006.01) |
| ***H03B 29/00*** | (2006.01) |
| ***H04R 3/00*** | (2006.01) |
| ***G10K 11/178*** | (2006.01) |

(52) U.S. Cl.

CPC ........... *H04R 3/002* (2013.01); *G10K 11/178* (2013.01); *G10K 11/1788* (2013.01); *G10K 11/1786* (2013.01); *G10K 2210/1282* (2013.01)

(58) Field of Classification Search

CPC ............. G10K 11/178; G10K 11/1782; G10K 11/1784; G10K 11/1786; G10K 11/1788; G10K 2210/128; G10K 2210/1282; G10K 2210/12821; G10K 2210/12822

USPC ....................................... 381/71.1–71.14, 86

See application file for complete search history.

(56) References Cited

U.S. PATENT DOCUMENTS

| | | | | | |
|---|---|---|---|---|---|
| 8,194,873 | B2 * | 6/2012 | Pan | .................... H03H 21/0067 | 381/71.11 |
| 8,306,240 | B2 * | 11/2012 | Pan | ...................... G10K 11/178 | 381/13 |
| 8,335,318 | B2 * | 12/2012 | Pan | .................... G10K 11/1782 | 381/56 |
| 8,355,512 | B2 * | 1/2013 | Pan | ...................... G10K 11/178 | 381/71.11 |

OTHER PUBLICATIONS

CN Office Action dated Jan. 29, 2012 for CN Application No. 200780022760.0.

* cited by examiner

*Primary Examiner* — Xu Mei
(74) *Attorney, Agent, or Firm* — Bose Corporation

(57) ABSTRACT

An active noise reduction system using adaptive filters. A method of operation the active noise reduction system includes smoothing a stream of leakage factors. The frequency of a noise reduction signal may be related to the engine speed of an engine associated with the system within which the active noise reduction system is operated. The engine speed signal may be a high latency signal and may be obtained by the active noise reduction system over audio entertainment circuitry.

10 Claims, 7 Drawing Sheets

ACTIVE NOISE REDUCTION ENGINE SPEED DETERMINING

CROSS-REFERENCE TO RELATED APPLICATIONS

This application is a continuation of U.S. patent application Ser. No. 11/426,512, filed Jun. 26, 2006, by Davis Pan, the entire contents of which are incorporated herein by reference.

BACKGROUND

This specification describes an active noise reduction system using adaptive filters. Active noise control is discussed generally in S. J. Elliot and P. A. Nelson, "Active Noise Control" IEEE Signal Processing Magazine, October 1993.

SUMMARY

In one aspect of the invention a method for operating an active noise reduction system includes providing filter coefficients of an adaptive filter in response to a noise signal; determining leakage factors associated with the filter coefficients; smoothing the leakage factors to provide smoothed leakage factors; applying the smoothed leakage factors to the filter coefficients to provide modified filter coefficients and, responsive to the modified filter coefficients, providing an active noise reduction signal characterized by a magnitude. The determining may be responsive to a triggering condition. The triggering condition may include the result of comparing the magnitude of the active noise reduction signal in a first spectral band with a first threshold. The triggering condition may include the result of comparing the magnitude of the active noise reduction signal in a second spectral band with a second threshold. The second threshold may have a predetermined relationship to the first threshold. The first threshold may be related to causing a device to operate non-linearly. The triggering condition may include the result of monitoring the active noise reduction system to determine if a predefined event has occurred. The predefined event may be that an entertainment signal magnitude is within a predetermined range of a magnitude that causes a device to operate non-linearly. The predefined event may occur in an audio entertainment system. The audio entertainment system may be associated with a vehicle. The predefined event may be the deactivation of the active noise reduction system. The predefined event may be that a noise signal is above a threshold associated with non-linear operation of an input transducer.

The smoothing may include low pass filtering. Prior to the smoothing, the determining may include selecting one of a discrete number of predetermined values for the leakage factor. The discrete number may be two. The discrete number may be greater than two. The method may further include combining the active noise reduction signal with an audio entertainment signal. The audio entertainment signal may be associated with an audio system in an enclosed space. The enclosed space may be a vehicle cabin.

The noise reduction system may be configured to be installed in a vehicle.

The determining may be responsive to a plurality of triggering conditions. The leakage factor determining may include determining which of the plurality of triggering conditions exist; responsive to a determining that a first triggering condition exists, selecting a first leakage factor value; and responsive to a determining that a second triggering condition exists, selecting a second leakage factor value.

In another aspect of the invention, an active noise reduction system includes an adaptive filter, for providing an active noise reduction signal; a coefficient calculator, for providing filter coefficients for the adaptive filter; and a leakage adjuster comprising a data smoother to provide smoothed leakage factors to apply to the filter coefficients. The apparatus may include circuitry for comparing the active noise reduction signal magnitude to a threshold. The apparatus may further include monitoring circuitry for monitoring the active noise reduction system to determine if a predefined event has occurred. The leakage adjuster may be responsive to the monitoring circuitry. The apparatus may further include an audio entertainment system. The monitoring circuitry may include circuitry for monitoring the audio entertainment system to determine if an entertainment audio signal magnitude is within a predetermined range of a magnitude that causes a device to operate non-linearly. The monitoring circuitry may further include circuitry for determining if the active noise reduction system has been deactivated. The active noise reduction system may further include an input transducer for transducing periodic vibrational energy to a noise signal and the monitoring circuitry may include circuitry for determining if the magnitude of the noise signal is above a threshold associated with non-linear operation of the input transducer.

The data smoother may include a low pass filter. The leakage adjuster may be constructed and arranged to select one of a discrete number of values for the leakage factor.

The apparatus may further include an audio entertainment system for providing an audio entertainment signal; and a combiner for combining the noise reduction signal.

In another aspect of the invention, a method for operating an noise reduction system includes providing a stream of leakage factor values and smoothing the stream of leakage values to provide a smoothed stream of leakage factor values. The value of each of the stream of leakage valued may be selected from a discrete number of predefined values. The providing of each of the stream of leakage values may be responsive to a detectable condition of the active noise reduction system. The detectable condition may be that the active noise reduction system has been deactivated. The detectable condition may be that the active noise reduction system has generated an audio signal having a magnitude greater than a threshold magnitude. The detectable condition may be that the magnitude of a noise signal is above a threshold associated with non-linear operation of an input transducer. The providing of each of the stream of leakage values may include selecting a leakage factor value from a plurality of predetermined leakage factor values. The method may further include applying the smoothed stream of leakage factor values to coefficients of an adaptive filter of an active noise reduction system.

In another aspect of the invention, a method for operating an adaptive filter of an active noise reduction system in which the adaptive filter characterized by coefficients includes smoothing the stream of leakage factor values to provide smoothed leakage factor values and applying the smoothed leakage factor values to the coefficients to provide modified coefficient values. The stream of leakage factor values may include values selected from a discrete number of predetermined leakage factor values. The discrete number may be two. Providing the stream of leakage factors may include calculating leakage factor values.

In another aspect of the invention, a method for operating an active noise reduction system includes providing a first threshold amplitude for a noise reduction signal corresponding to a first noise amplitude limit for a first frequency; providing a second threshold amplitude for noise reduction signal corresponding to a second noise amplitude limit for a second frequency, wherein the second noise amplitude limit has a predetermined relationship to the first noise amplitude limit; calculating filter coefficients associated with adaptive filters associated with the noise reduction system to provide a noise reduction signal characterized by a magnitude; and determining, responsive to a comparing of the magnitude of the noise reduction signal to the first threshold amplitude at the first frequency and to the second threshold amplitude of the second frequency, leakage factors for modifying the filter coefficients. The second frequency may be a predetermined multiple of the first frequency. The second noise amplitude limit may be non-zero. The active noise reduction system may be associated with a sinusoidal noise source, such as an engine, which may be associated with a vehicle. The first frequency may be related to the frequency of the sinusoidal noise source, such as an engine associated with the sinusoidal noise source.

In another aspect of the invention, an active noise reduction system includes determining an amplitude of a first noise reduction signal characterized by a first frequency and providing a non-zero noise reduction amplitude limit for a second frequency, wherein the second frequency has a predetermined relationship to the first frequency and wherein the noise reduction amplitude limit has a predetermined relationship to the first amplitude. The method may further include, in response to a noise signal characterized by the second frequency and by an amplitude, providing filter coefficients of an adaptive filter to reduce the noise signal amplitude; in the event that the noise signal amplitude is greater than the noise reduction amplitude limit, applying a first leakage factor to the filter coefficients; and in the event that the noise signal amplitude is equal to or greater than the noise reduction amplitude limit, applying a second leakage factor to the filter coefficients.

The active noise reduction system may be associated with a sinusoidal noise source and the first frequency may be related to the vehicle. The sinusoidal noise source may be an engine, which may be associated with a vehicle. The method may further include nulling the first noise reduction signal.

In another aspect of the invention, a method for operating an active noise reduction system includes providing filter coefficients of an adaptive filter in response to a noise signal and determining leakage factors associated with the filter coefficients. The determining includes in response to a first triggering condition, providing a first leakage factor; in response to a second triggering condition, providing a second discrete leakage factor; and in the absence of the first triggering condition and the second triggering condition, providing a default leakage factor.

In another aspect of the invention, a method for operating an active noise reduction system includes receiving a high latency signal representative of engine speed; providing a noise reduction audio signal at a reference frequency, the reference frequency related to the engine speed; and generating a noise reduction audio signal at a frequency corresponding to a predetermined multiple of the reference frequency.

The method may further include transducing acoustic energy in an enclosed space to provide a noise signal representative of the noise in the enclosed space, and determining, responsive to the noise signal, a phase and a magnitude of the noise reduction signal. The determining the phase and magnitude of the noise reduction signal may be performed by circuitry comprising an adaptive filter. The enclosed space may be a vehicle cabin.

In another aspect of the invention, a method for operating an active noise reduction system includes receiving from a bus associated with an audio entertainment system a signal representative of engine speed and responsive to the signal representative of engine speed, generating a noise reduction audio signal having a frequency related to the engine speed. The method may further include receiving from the bus, an entertainment audio signal. The receiving the signal representative of engine speed may include receiving a high latency signal. The method may further include processing the entertainment audio signal to provide a processed entertainment audio signal and combining the processed entertainment audio signal with the noise reduction audio signal. The method may further include receiving from the bus an entertainment system control signal. The method may further include receiving from the bus, an entertainment audio signal. The method may still further include processing the entertainment audio signal to provide a processed entertainment audio signal and combining the processed entertainment audio signal with the noise reduction audio signal.

In another aspect of the invention, an audio system includes an input element for receiving a signal representative of engine speed and entertainment audio control signal circuitry for generating a noise reduction signal of a frequency related to the signal representative of engine speed. The audio system may further include audio signal processing circuitry for processing the entertainment audio signal to provide a processed entertainment audio signal; and an acoustic driver, for radiating acoustic energy corresponding to the noise cancellation signal and also corresponding to the processed entertainment audio signal Other features, objects, and advantages will become apparent from the following detailed description, when read in connection with the following drawing, in which:

DETAILED DESCRIPTION

Figure 1A:
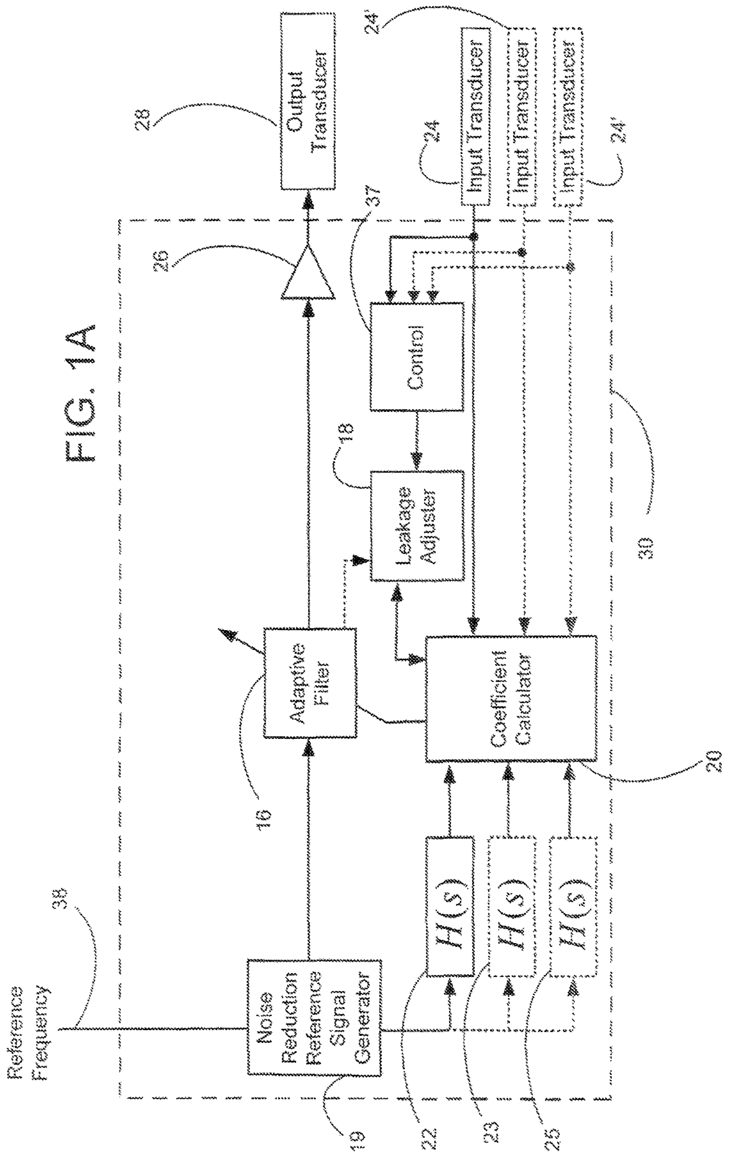
FIG. 1A is a block diagram of an active noise reduction system.

Though the elements of several views of the drawing may be shown and described as discrete elements in a block diagram and may be referred to as "circuitry", unless otherwise indicated, the elements may be implemented as one of, or a combination of, analog circuitry, digital circuitry, or one or more microprocessors executing software instructions. The software instructions may include digital signal processing (DSP) instructions. Unless otherwise indicated, signal lines may be implemented as discrete analog or digital signal lines. Multiple signal lines may be implemented as one discrete digital signal line with appropriate signal processing to process separate streams of audio signals, or as elements of a wireless communication system. Some of the processing operations may be expressed in terms of the calculation and application of coefficients. The equivalent of calculating and applying coefficients can be performed by other analog or DSP techniques and are included within the scope of this patent application. Unless otherwise indicated, audio signals may be encoded in either digital or analog form; conventional digital-to-analog and analog-to-digital converters may not be shown in circuit diagrams. This specification describes an active noise reduction system. Active noise reduction systems are typically intended to eliminate undesired noise (i.e. the goal is zero noise). However in actual noise reduction systems undesired noise is attenuated, but complete noise reduction is not attained. In this specification "driving toward zero" means that the goal of the active noise reduction system is zero noise, though it is recognized that actual result is significant attenuation, not complete elimination.

Referring to FIG. 1A, there is shown a block diagram of an active noise reduction system. Communication path 38 is coupled to noise reduction reference signal generator 19 for presenting to the noise reduction reference signal generator a reference frequency. The noise reduction reference signal generator is coupled to filter 22 and adaptive filter 16. The filter 22 is coupled to coefficient calculator 20. Input transducer 24 is coupled to control block 37 and to coefficient calculator 20, which is in turn bidirectionally coupled to leakage adjuster 18 and adaptive filter 16. Adaptive filter 16 is coupled to output transducer 28 by power amplifier 26. Control block 37 is coupled to leakage adjuster 18. Optionally, there may be additional input transducers 24' coupled to coefficient calculator 20, and optionally, the adaptive filter 16 may be coupled to leakage adjuster 18. If there are additional input transducers 24', there typically will be a corresponding filter 23, 25.

In operation, a reference frequency, or information from which a reference frequency can be derived, is provided to the noise reduction reference signal generator 19. The noise reduction reference signal generator generates a noise reduction signal, which may be in the form of a periodic signal, such as a sinusoid having a frequency component related to the engine speed, to filter 22 and to adaptive filter 16. Input transducer 24 detects periodic vibrational energy having a frequency component related to the reference frequency and transduces the vibrational energy to a noise signal, which is provided to coefficient calculator 20. Coefficient calculator 20 determines coefficients for adaptive filter 16. Adaptive filter 16 uses the coefficients from coefficient calculator 20 to modify the amplitude and/or phase of the noise cancellation reference signal from noise reduction reference signal generator 19 and provides the modified noise cancellation signal to power amplifier 26. The noise reduction signal is amplified by power amplifier 26 and transduced to vibrational energy by output transducer 28. Control block 37 controls the operation of the active noise reduction elements, for example by activating or deactivating the active noise reduction system or by adjusting the amount of noise attenuation.

The adaptive filter 16, the leakage adjuster 18, and the coefficient calculator 20 operate repetitively and recursively to provide a stream of filter coefficients that cause the adaptive filter 16 to modify a signal that, when transduced to periodic vibrational energy, attenuates the vibrational energy detected by input transducer 24. Filter 22, which can be characterized by transfer function H(s), compensates for effects on the energy transduced by input transducer 24 of components of the active noise reduction system (including power amplifier 26 and output transducer 28) and of the environment in which the system operates.

Input transducer(s) 24, 24' may be one of many types of devices that transduce vibrational energy to electrically or digitally encoded signals, such as an accelerometer, a microphone, a piezoelectric device, and others. If there is more than one input transducer, 24, 24', the filtered inputs from the transducers may be combined in some manner, such as by averaging, or the input from one may be weighted more heavily than the others. Filter 22, coefficient calculator 20, leakage adjuster 18, and control block 37 may be implemented as instructions executed by a microprocessor, such as a DSP device. Output transducer 28 can be one of many electromechanical or electroacoustical devices that provide periodic vibrational energy, such as a motor or an acoustic driver.

Figure 1B:
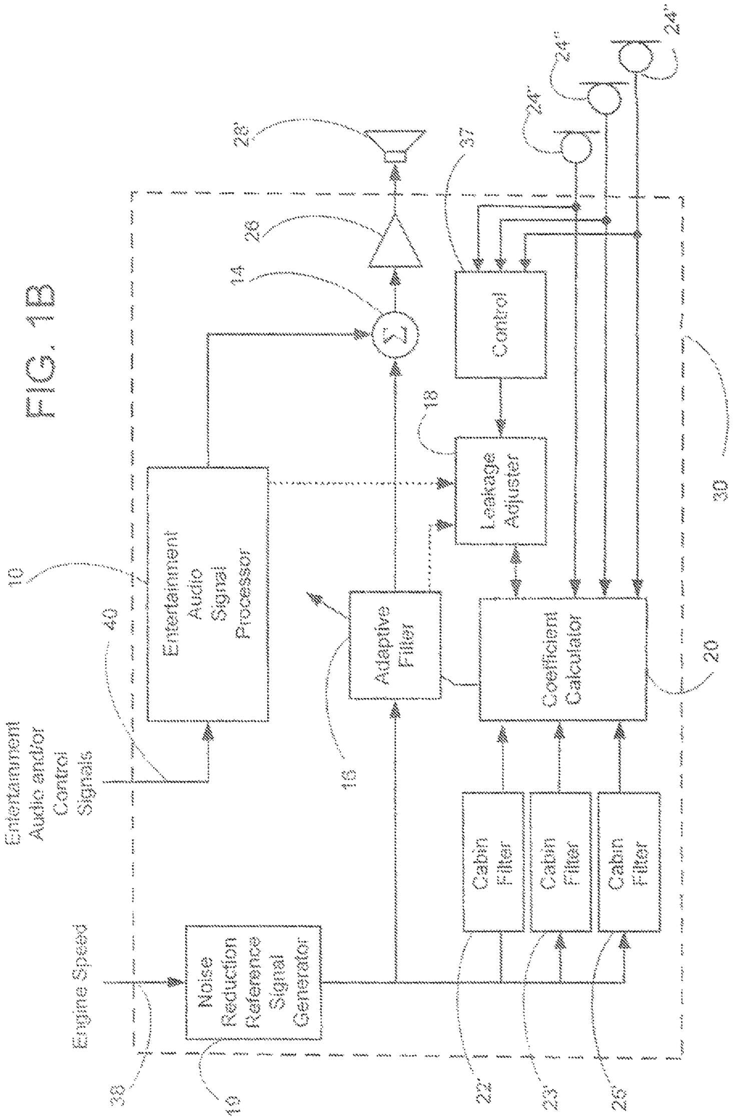
FIG. 1B is a block diagram including elements of the active noise reduction system of FIG. 1A implemented as an active acoustic noise reduction system in a vehicle.

Referring to FIG. 1B, there is shown a block diagram including elements of the active noise reduction system of FIG. 1A. The active noise reduction system of FIG. 1B is implemented as an active acoustic noise reduction system in an enclosed space. FIG. 1B is described as configured for a vehicle cabin, but and also be configured for use in other enclosed spaces, such as a room or control station. The system of FIG. 1B also includes elements of an audio entertainment or communications system, which may be associated with the enclosed space. For example, if the enclosed space is a cabin in a vehicle, such as a passenger car, van, truck, sport utility vehicle, construction or farm vehicle, military vehicle, or airplane, the audio entertainment or communications system may be associated with the vehicle. Entertainment audio signal processor 10 is communicatingly coupled to signal line 40 to receive an entertainment audio signal and/or an entertainment system control signal, and is coupled to combiner 14 and may be coupled to leakage adjuster 18. Noise reduction reference signal generator 19 is communicatingly coupled to signal line 38 and to adaptive filter 16 and cabin filter 22', which corresponds to the filter 22 of FIG. 1A. Adaptive filter 16 is coupled to combiner 14, to coefficient calculator 20, and optionally may be directly coupled to leakage adjuster 18. Coefficient calculator 20 is coupled to cabin filter 22', to leakage adjuster 18, and to microphones 24", which correspond to the input transducers 24, 24' of FIG. 1A. Combiner 14 is coupled to power amplifier 26 which is coupled to acoustic driver 28', which corresponds to output transducer 28 of FIG. 1A. Control block 37 is communicatingly coupled to leakage adjuster 18 and to microphones 24". In many vehicles, entertainment audio signal processor 10 is coupled to a plurality of combiners 14, each of which is coupled to a power amplifier 26 and an acoustic driver 28'.

Each of the plurality of combiners 14, power amplifiers 26, and acoustic drivers 28' may be coupled, through elements such as amplifiers and combiners to one of a plurality of adaptive filters 16, each of which has associated with it a leakage adjuster 18, a coefficient calculator 20, and a cabin filter 22. A single adaptive filter 16, associated leakage adjuster 18, and coefficient calculator 20 may modify noise cancellation signals presented to more than one acoustic driver. For simplicity, only one combiner 14, one power amplifier 26, and one acoustic driver 28' are shown. Each microphone 24" may be coupled to more than one coefficient calculator 20.

All or some of the entertainment audio signal processor 10, the noise reduction reference signal generator 19, the adaptive filter 16, the cabin filter 22', the coefficient calculator 20 the leakage adjuster 18, the control block 37, and the combiner 14 may be implemented as software instructions executed by one or more microprocessors or DSP chips. The power amplifier 26 and the microprocessor or DSP chip may be components of an amplifier 30.

In operation, some of the elements of FIG. 1B operate to provide audio entertainment and audibly presented information (such as navigation instructions, audible warning indicators, cellular phone transmission, operational information [for example, low fuel indication], and the like) to occupants of the vehicle. An entertainment audio signal from signal line 40 is processed by entertainment audio signal processor 10. A processed audio signal is combined with an active noise reduction signal (to be described later) at combiner 14. The combined signal is amplified by power amplifier 26 and transduced to acoustic energy by acoustic driver 28'.

Some elements of the device of FIG. 1B operate to actively reduce noise in the vehicle compartment caused by the vehicle engine and other noise sources. The engine speed, which is typically represented as pulses indicative of the rotational speed of the engine, also referred to as revolutions per minute or RPM, is provided to noise reduction reference signal generator 19, which determines a reference frequency according to $$f(\text{Hz}) = \frac{\text{engine\_speed(rpm)}}{60}.$$

The reference frequency is provided to cabin filter 22'. The noise reduction reference signal generator 19 generates a noise cancellation signal, which may be in the form of a periodic signal, such as a sinusoid having a frequency component related to the engine speed. The noise cancellation signal is provided to adaptive filter 16 and in turn to cabin filter 22'. Microphone 24" transduces acoustic energy, which may include acoustic energy corresponding to entertainment audio signals, in the vehicle cabin to a noise audio signal, which is provided to the coefficient calculator 20. The coefficient calculator 20 modifies the coefficients of adaptive filter 16. Adaptive filter 16 uses the coefficients to modify the amplitude and/or phase of the noise cancellation signal from noise reduction reference signal generator 19 and provides the modified noise cancellation signal to signal combiner 14. The combined effect of some electro-acoustic elements (for example, acoustic driver 28', power amplifier 26, microphone 24" and of the environment within which the noise reduction system operates) can be characterized by a transfer function H(s). Cabin filter 22' models and compensates for the transfer function H(s). The operation of the leakage adjuster 18 and control block 37 will be described below.

The adaptive filter 16, the leakage adjuster 18, and the coefficient calculator 20 operate repetitively and recursively to provide a stream of filter coefficients that cause the adaptive filter 16 to modify an audio signal that, when radiated by the acoustic driver 28', drives the magnitude of specific spectral components of the signal detected by microphone 24" to some desired value. The specific spectral components typically correspond to fixed multiples of the frequency derived from the engine speed. The specific desired value to which the magnitude of the specific spectral components is to be driven may be zero, but may be some other value as will be described below.

The elements of FIGS. 1A and 1B may also be replicated and used to generate and modify noise reduction signals for more than one frequency. The noise reduction signal for the other frequencies is generated and modified in the same manner as described above.

The content of the audio signals from the entertainment audio signal source includes conventional audio entertainment, such as for example, music, talk radio, news and sports broadcasts, audio associated with multimedia entertainment and the like, and, as stated above, may include forms of audible information such as navigation instructions, audio transmissions from a cellular telephone network, warning signals associated with operation of the vehicle, and operational information about the vehicle. The entertainment audio signal processor may include stereo and/or multi-channel audio processing circuitry. Adaptive filter 16 and coefficient calculator 20 together may be implemented as one of a number of filter types, such as an n-tap delay line; a Leguerre filter; a finite impulse response (FIR) filter; and others. The adaptive filter may use one of a number of types of adaptation schemes, such as a least mean squares (LMS) adaptive scheme; a normalized LMS scheme; a block LMS scheme; or a block discrete Fourier transform scheme; and others. The combiner 14 is not necessarily a physical element, but rather may be implemented as a summation of signals.

Though shown as a single element, the adaptive filter 16 may include more than one filter element. In some embodiments of the system of FIG. 1B, adaptive filter 16 includes two FIR filter elements, one each for a sine function and a cosine function with both sinusoid inputs at the same frequency, each FIR filter using an LMS adaptive scheme with a single tap, and a sample rate which may be related to the audio frequency sampling rate r (for example $$\left(\text{for example } \frac{r}{28}\right).$$

). Suitable adaptive algorithms for use by the coefficient calculator 20 may be found in *Adaptive Filter Theory, 4th Edition* by Simon Haykin, ISBN 0130901261. Leakage adjuster 18 will be described below.

Figure 2A:
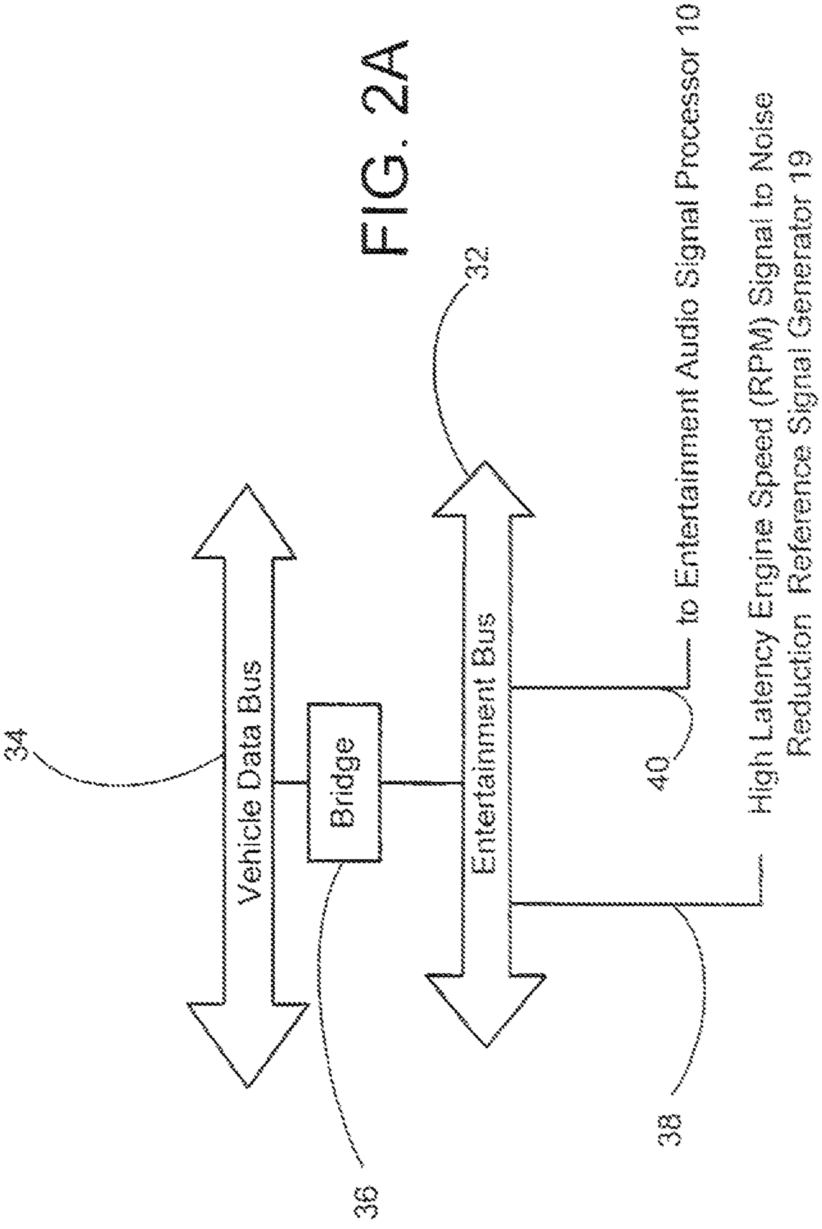
FIG. 2A is a block diagram of a delivery system of the reference frequency and an implementation of the delivery system of the entertainment audio signal of FIG. 1B.

FIG. 2A is a block diagram showing devices that provide the engine speed to noise reduction reference signal generator 19 and that provide the audio entertainment signal to audio signal processor 10. The audio signal delivery elements may include an entertainment bus 32 coupled to audio signal processor 10 of FIG. 1B by signal line 40 and further coupled to noise reduction reference signal generator 19 by signal line 38. The entertainment bus may be a digital bus that transmits digitally encoded audio signals among elements of a vehicle audio entertainment system. Devices such as a CD player, an MP3 player, a DVD player or similar devices or a radio receiver (none of which are shown) may be coupled to the entertainment bus 32 to provide an entertainment audio signal. Also coupled to entertainment bus 32 may be sources of audio signals representing information such as navigation instructions, audio transmissions from a cellular telephone network, warning signals associated with operation of the vehicle, and other audio signals.

The engine speed signal delivery elements may include a vehicle data bus 34 and a bridge 36 coupling the vehicle data bus 34 and the entertainment bus 32. The example has been described with reference to a vehicle with an entertainment system; however the system of FIG. 2A may be implemented with noise reducing systems associated with other types of sinusoidal noise sources, for example a power transformer. The system may also be implemented in noise reducing systems that do not include an entertainment system, by providing combinations of buses, signal lines, and other signal transmission elements that result in latency characteristics similar to the system of FIG. 2A.

In operation, the entertainment bus 32 transmits audio signals and/or control and/or status information for elements of the entertainment system. The vehicle data bus 34 may communicate information about the status of the vehicle, such as the engine speed. The bridge 36 may receive engine speed information and may transmit the engine speed information to the entertainment bus, which in turn may transmit a high latency engine speed signal to the noise reduction reference signal generator 19. As will be described more fully below, in FIGS. 2A and 2B, the terms "high latency" and "low latency" apply to the interval between the occurrence of an event, such as a change in engine speed, and the arrival of an information signal indicating the change in engine speed at the active noise reduction system. The buses may be capable of transmitting signals with low latency, but the engine speed signal may be delivered with high latency, for example because of delays in the bridge 36.

Figure 2B:
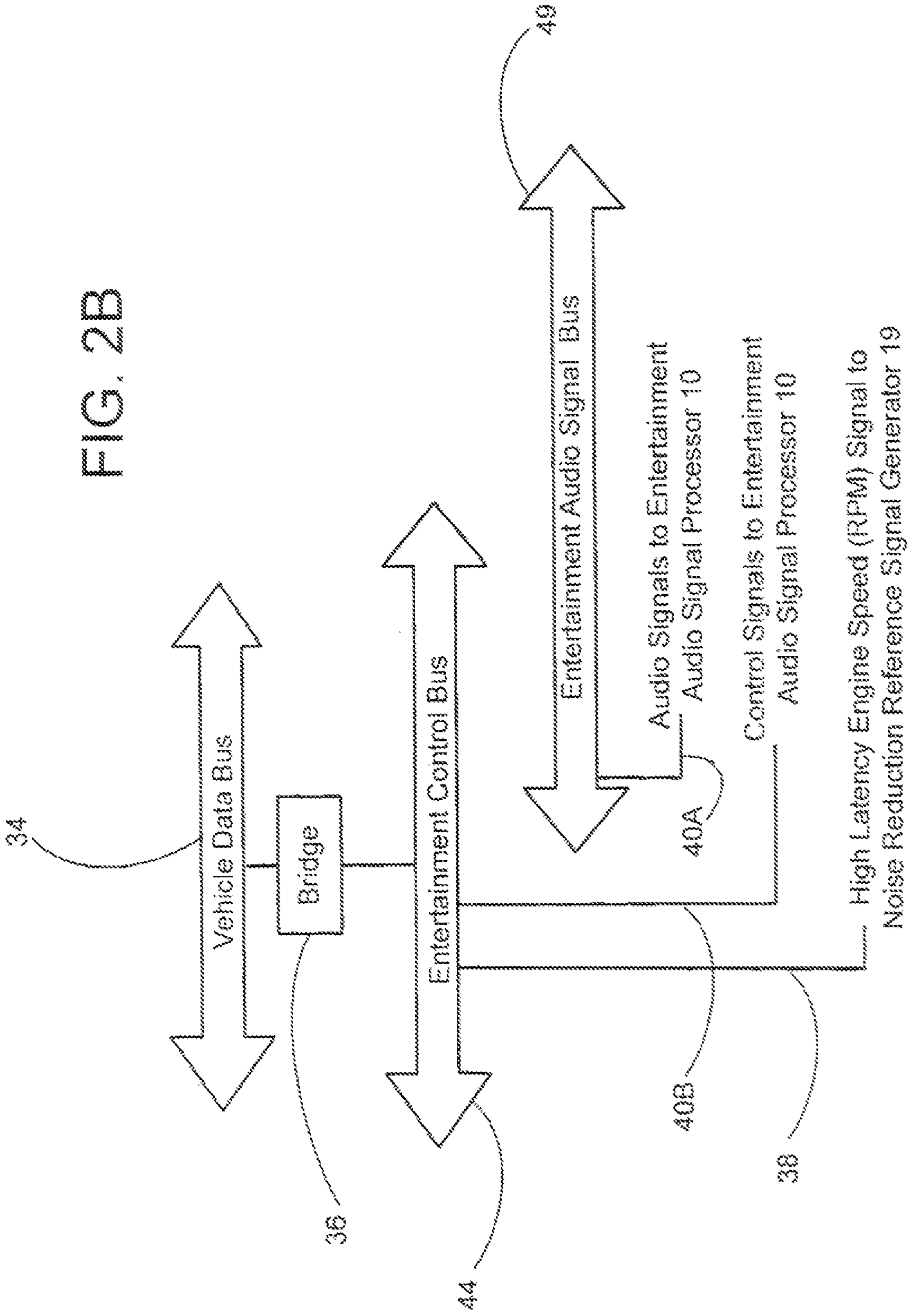
FIG. 2B is a block diagram of another implementation of the delivery system of the reference frequency and the delivery system of the entertainment audio signal of FIG. 1B.

FIG. 2B illustrates another implementation of the signal delivery elements of the engine speed signal and the signal delivery elements of the entertainment audio signal of FIG. 1B. The entertainment audio signal delivery elements include entertainment audio signal bus 49 coupled to audio signal processor 10 of FIG. 1B by signal line 40A. Entertainment control bus 44 is coupled to audio entertainment processor 10 of FIG. 1B by signal line 40B. The engine speed signal delivery elements include the vehicle data bus 34 coupled to an entertainment control bus 44 by bridge 36. The entertainment control bus 44 is coupled to noise reduction reference signal generator 19 by signal line 38.

The embodiment of FIG. 2B operates similarly to the embodiment of FIG. 2A, except that the high latency engine speed signal is transmitted from the bridge 36 to the entertainment control bus 44 and then to the noise reduction reference signal generator 19. Audio signals are transmitted from the entertainment audio signal bus 49 to entertainment audio signal processor 10 over signal line 40A. Entertainment control signals are transmitted from entertainment control bus 44 to entertainment audio signal processor 10 of FIG. 1 by signal line 40B. Other combinations of vehicle data buses, entertainment buses, entertainment control buses, entertainment audio signal buses, and other types of buses and signal lines, depending on the configuration of the vehicle, may be used to provide the engine speed signal to reference signal generator 19 and the audio entertainment signal to entertainment signal processor 20.

Conventional engine speed signal sources include a sensor, sensing or measuring some engine speed indicator such as crankshaft angle, intake manifold pressure, ignition pulse, or some other condition or event. Sensor circuits are typically low latency circuits but require the placement of mechanical, electrical, optical or magnetic sensors at locations that may be inconvenient to access or may have undesirable operating conditions, for example high temperatures, and also require communications circuitry, typically a dedicated physical connection, between the sensor and noise reduction reference signal generator 19 and/or adaptive filter 16 and/or cabin filter 22'. The vehicle data bus is typically a high speed, low latency bus that includes information for controlling the engine or other important components of the vehicle. Interfacing to the vehicle data bus adds complexity to the system, and in addition imposes constraints on the devices that interface to the vehicle data bus so that the interfacing device does not interfere with the operation of important components that control the operation of the vehicle. Engine speed signal delivery systems according to FIGS. 2A and 2B are advantageous over other engine speed signal sources and engine speed signal delivery systems because they permit active noise reduction capability without requiring any dedicated components such as dedicated signal lines. Arrangements according to FIGS. 2A and 2B are further advantageous because the vehicle data bus 34, bridge 36, and one or both of the entertainment bus 32 of FIG. 2A or the entertainment control bus 44 of FIG. 2B are present in many vehicles so no additional signal lines for engine speed are required to perform active noise reduction. Arrangements according to FIG. 2A or 2B also may use existing physical connection between the entertainment bus 32 or entertainment control bus 44 and the amplifier 30 and require no additional physical connections, such as pins or terminals for adding active noise reduction capability. Since entertainment bus 32 or entertainment control bus 44 may be implemented as a digital bus, the signal lines 38 and 40 of FIG. 2A and signal lines 38, 40A and 40B of FIG. 2B may be implemented as a single physical element, for example a pin or terminal, with suitable circuitry for routing the signals to the appropriate component.

An engine speed signal delivery system according to FIGS. 2A and 2B may be a high latency delivery system, due to the bandwidth of the entertainment bus, the latency of the bridge 36, or both. "High latency," in the context of this specification, means a latency between the occurrence of an event, such as an ignition event or a change in engine speed, and the arrival at noise reduction reference signal generator 19 of a signal indicating the occurrence of the event, of 10 ms or more.

An active noise reduction system that can operate using a high latency signal is advantageous because providing a low latency signal to the active noise reduction system is typically more complicated, difficult, and expensive than using an already available high latency signal.

Figure 3A:
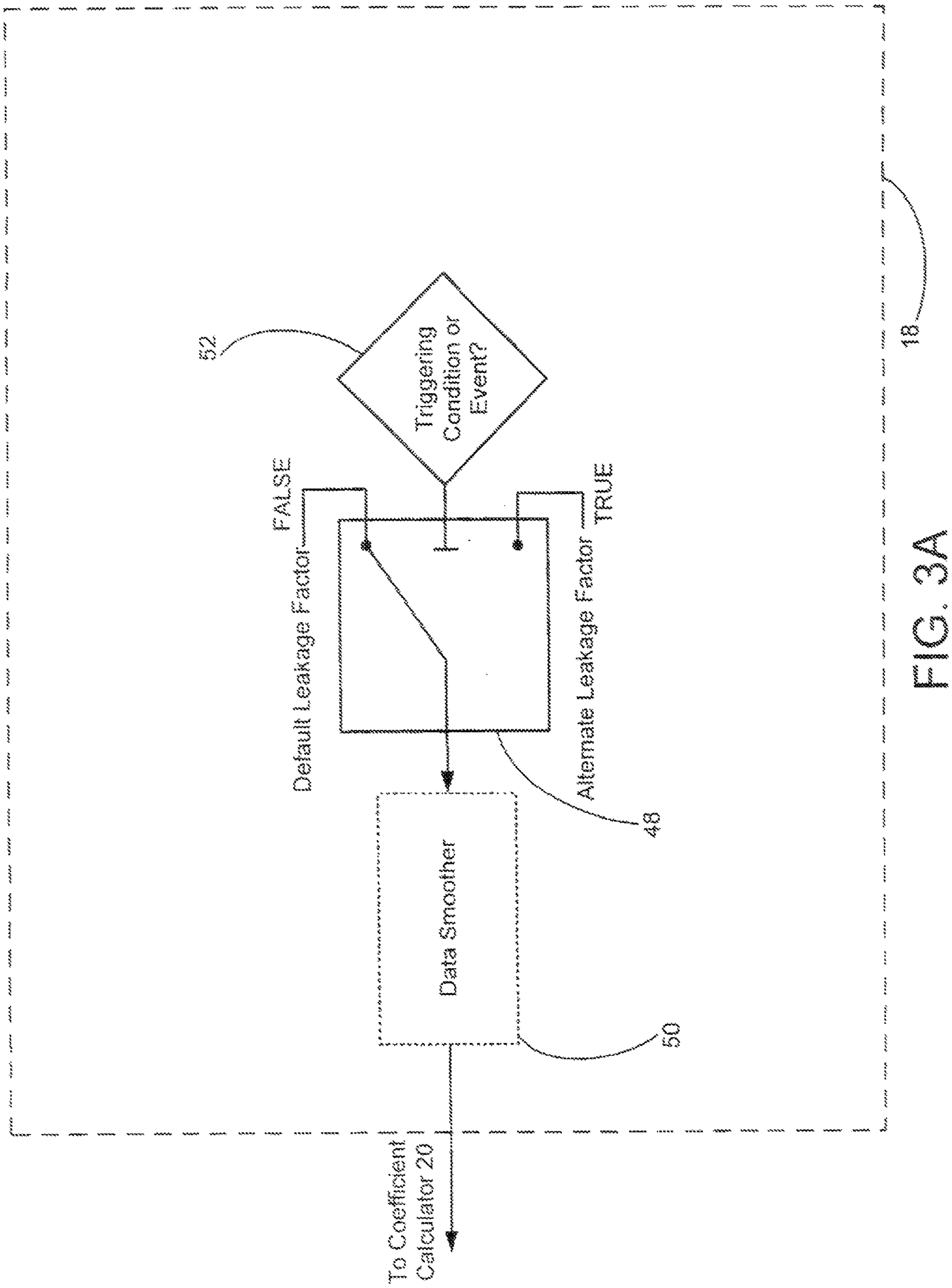
FIG. 3A is a block diagram showing the logical flow of the operation of the leakage adjuster of FIGS. 1A and 1B.

The leakage adjuster 18 will now be described in more detail. FIG. 3A is a block diagram showing the logical flow of the operation of the leakage adjuster 18. The leakage adjuster selects a leakage factor to be applied by the coefficient calculator 20. A leakage factor is a factor $\alpha$ applied in adaptive filters to an existing coefficient value when the existing coefficient value is updated by an update amount; for example $$(\text{new\_value})=\alpha(\text{old\_value})+(\text{update\_amount})$$

Information on leakage factors may be found in Section 13.2 of *Adaptive Filter Theory* by Simon Haykin, $4^{th}$ Edition, ISBN 0130901261. Logical block 52 determines if a predefined triggering event has occurred, or if a predefined triggering condition exists, that may cause it to be desirable to use an alternate leakage factor. Specific examples of events or conditions will be described below. If the value of the logical block 52 is FALSE, the default leakage factor is applied at leakage factor determination logical block 48. If the value of logical block 52 is TRUE, an alternate, typically lower, leakage factor may be applied at leakage factor determination logical block 48. The alternate leakage factor may be calculated according to an algorithm, or may operate by selecting a leakage factor value from a discrete number of predetermined leakage factor values based on predetermined criteria. The stream of leakage factors may optionally be smoothed (block 50), for example by low pass filtering, to prevent abrupt changes in the leakage factor that have undesirable results. The low pass filtering causes leakage factor applied by adaptive filter 16 to be bounded by the default leakage factor and the alternate leakage factor. Other forms of smoothing may include slew limiting or averaging over time.

Figure 3B:
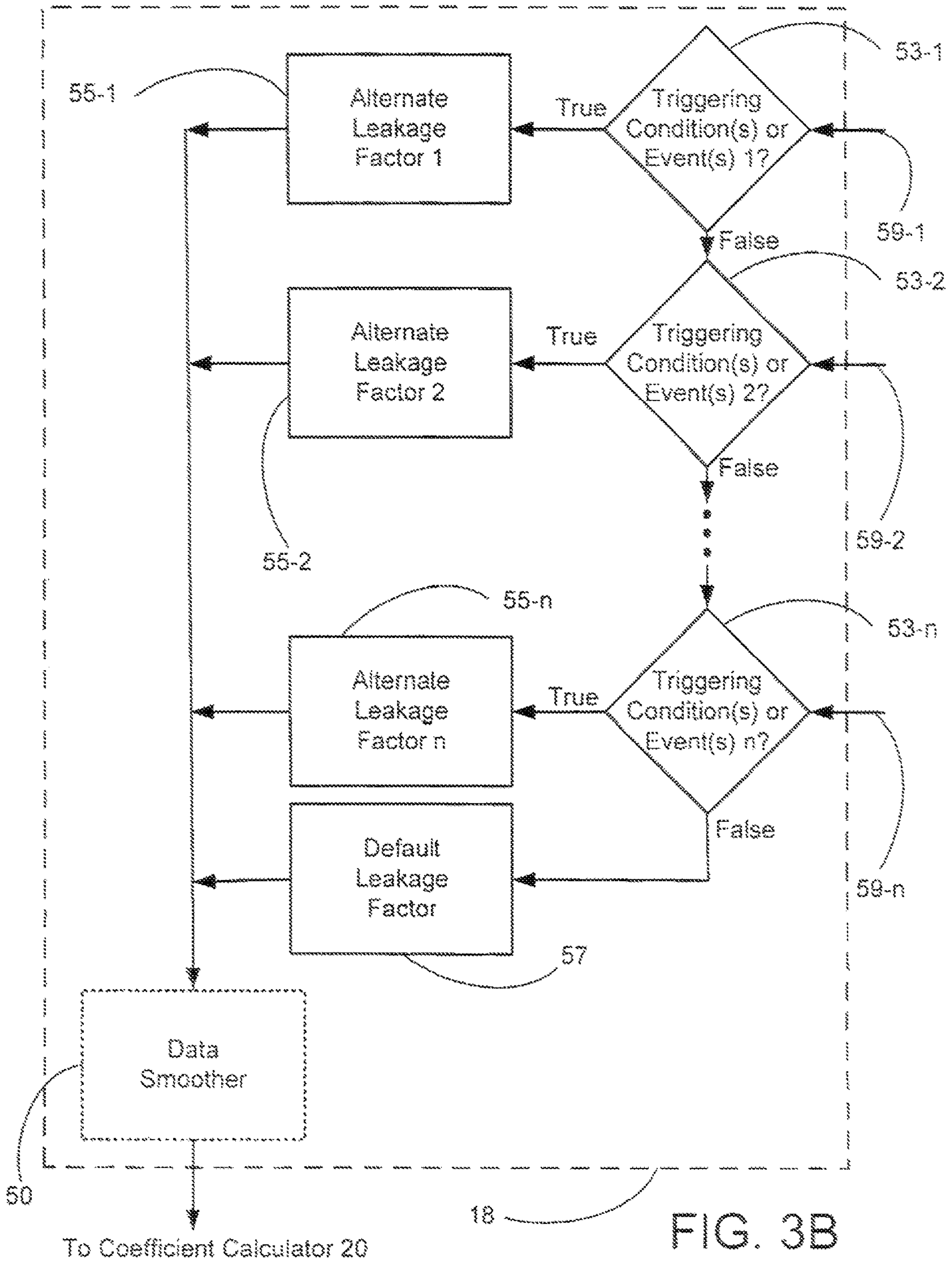
FIG. 3B is a block diagram showing the logical flow of the operation of another implementation of a leakage adjuster, permitting a more complex leakage adjustment scheme.

FIG. 3B is a block diagram showing the logical flow of the operation of a leakage adjuster 18 permitting more than one, for example n, alternate leakage factor and permitting the n alternate leakage factors to be applied according to a predetermined priority. At logical block 53-1, it is determined if the highest priority triggering conditions exist or events have occurred. If the value of logical block 53-1 is TRUE, the leakage factor associated with the triggering conditions and events of logical block 53-1 is selected at logical block 55-1 and provided to the coefficient calculator 20 through a data smoother 50, if present. If the value of logical block 53-1 is FALSE, it is determined at logical block 53-2 if the second highest priority triggering conditions exist or events have occurred. If the value of logical block 53-2 is TRUE, the leakage factor associated with the triggering conditions and events of logical block 53-2 is selected at logical block 55-2 and provided to the coefficient calculator 20 through the data smoother 50, if present. If the value of logical block 53-2 is FALSE, then it is determined if the next highest priority triggering conditions exist or events have occurred. The process proceeds until at logical block **53-*n*, it is determined if the lowest (or nth highest) priority triggering conditions exist or events have occurred. If the value of logical block 53-*n* is TRUE, the leakage factor associated with the lowest priority triggering conditions or events is selected at logical block 55-*n* and provided to the coefficient calculator 20 through the data smoother 50, if present. If the value of logical block 53-*n* is FALSE, at logical block 57 the default leakage factor is selected and provided to the coefficient calculator 20 through the data smoother 50**, if present.

In one implementation of FIG. 3B, there are 2 sets of triggering conditions and events and two associated leakage factors (n=2). The highest priority triggering conditions or events include the system being deactivated, the frequency of the noise reduction signal being out of the spectral range of the acoustic driver, or the noise detected by an input transducer such as a microphone having a magnitude that would induce non-linear operation, such as clipping. The leakage factor associated with the highest priority triggering conditions is 0.1. The second highest priority triggering conditions or events include the cancellation signal magnitude from adaptive filter 16 exceeding a threshold magnitude, the magnitude of the entertainment audio signal approaching (for example coming within a predefined range, such as 6 dB) the signal magnitude at which one of more electro-acoustical elements of FIG. 1B, such as the power amplifier 26 or the acoustic driver 28' may operate non-linearly, or some other event occurring that may result in an audible artifact, such as a click or pop, or distortion. Events that may cause an audible artifact, such as a click, pop, or distortion may include output levels being adjusted or the noise reduction signal having an amplitude or frequency that is known to cause a buzz or rattle in the acoustic driver 28 or some other component of the entertainment audio system. The leakage factor associated with the second highest priority triggering conditions and events is 0.5. The default leakage factor is 0.999999.

Logical blocks 53-1-**53-*n* receive indication that a triggering event has or is about to occur or that a triggering condition exists from an appropriate element of FIG. 1A or 1B, as indicated by arrows 59-1-59-*n*. The appropriate element may be control block 37 of FIG. 1B; however the indication may come from other elements. For example if the predefined event is that the magnitude of the entertainment audio signal approaches a non-linear operating range of one of the elements of FIG. 1B, the indication may originate in the entertainment audio signal processor 10** (not shown in this view).

The processes of FIGS. 3A and 3B are typically implemented by digital signal processing instructions on a DSP processor. Specific values for the default leakage factor and the alternate leakage factor may be determined empirically. Some systems may not apply a leakage factor in default situations. Since the leakage factor is multiplicative, not applying a leakage factor is equivalent to applying a leakage factor of 1. Data smoother 50 may be implemented, for example as a first order lowpass filter with a tunable frequency cutoff that may be set, for example, at 20 Hz.

An active noise reduction system using the devices and methods of FIGS. 1A, 1B, 3A, and 3B is advantageous because it significantly reduces the number of occurrences of audible clicks or pops, and because it significantly reduces the number of occurrences of distortion and non-linearities.

The active noise reduction system may control the magnitude of the noise reduction audio signal, to avoid over-driving the acoustic driver or for other reasons. One of those other reasons may be to limit the noise present in the enclosed space to a predetermined non-zero target value, or in other words to permit a predetermined amount of noise in the enclosed space. In some instances it may be desired to cause the noise in the enclosed space to have a specific spectral profile to provide a distinctive sound or to achieve some effect.

Figure 4:
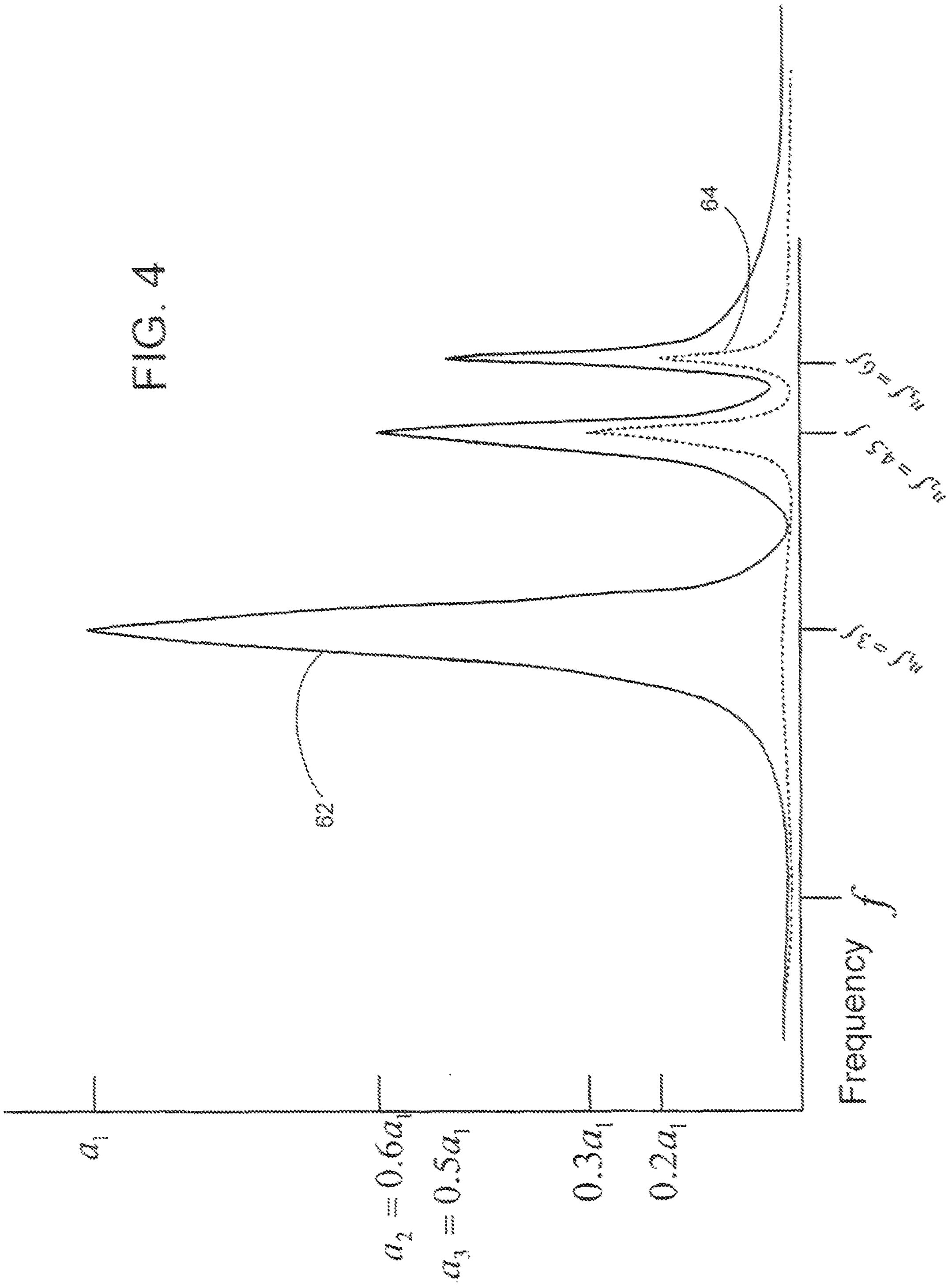
FIG. 4 is a frequency response curve illustrating an example of a specific spectral profile.

FIG. 4 illustrates an example of a specific spectral profile. For simplicity, the effect of the room and characteristics of the acoustic driver 28 will be omitted from the explanation. The effect of the room is modeled by the filter 22 of FIG. 1A or the cabin filter 22' of FIG. 1B. An equalizer compensates for the acoustic characteristics of the acoustic driver. Additionally, to facilitate describing the profile in terms of ratios, the vertical scale of FIG. 4 is linear, for example volts of the noise signal from microphone 24". The linear scale can be converted to a non-linear scale, such as dB, by standard mathematical techniques.

In FIG. 4, the frequency f may be related to the engine speed, for example as $$f(\text{Hz}) = \frac{\text{engine\_speed(rpm)}}{60}.$$

Curve 62 represents the noise signal without the active noise cancellation elements operating. Curve 64 represents the noise signal with the active noise cancellation elements operating. Numbers $n_1$, $n_2$, and $n_3$ may be fixed numbers so that $n_1f$, $n_2f$, and $n_3f$ are fixed multiples off. Factors $n_1$, $n_2$, and $n_3$ may be integers so that frequencies $n_1f$, $n_2f$, and $n_3f$ can conventionally be described as "harmonics", but do not have to be integers. The amplitudes $a_1$, $a_2$, and $a_3$ at frequencies $n_1f$, $n_2f$, and $n_3f$ may have a desired characteristic relationship, for example $a_2=0.6\ a_1$ or $$\frac{a_2}{a_1}=0.6$$

and $a_3=0.5\ a_1$ or $$\frac{a_3}{a_1}=0.5.$$

These relationships may vary as a function of frequency.

There may be little acoustic energy at frequency f. It is typical for the dominant noise to be related to the cylinder firings, which for a four cycle, six cylinder engine occurs three times each engine rotation, so the dominant noise may be at the third harmonic of the engine speed, so in this example $n_1=3$. It may be desired to reduce the amplitude at frequency 3f ($n_1=3$) as much as possible because noise at frequency 3f is objectionable. To achieve some acoustic effect, it may be desired to reduce the amplitude at frequency 4.5f (so in this example $n_2=4.5$) but not as far as possible, for example to amplitude 0.5 $a_2$. Similarly, it may be desired to reduce the amplitude at frequency 6f (so in this example $n_3=6$) to, for example $0.4a_3$. In this example, referring to FIG. 1B, noise reduction reference signal generator 19 receives the engine speed from the engine speed signal delivery system and generates a noise reduction reference signal at frequency 3f. The coefficient calculator 16 determines filter coefficients appropriate to provide a noise reduction audio signal to drive the amplitude at frequency 3f toward zero, thereby determining amplitude $a_1$. In instances in which the noise at frequency 3f is not objectionable, but rather is desired to achieve the acoustic effect, the adaptive filter may null the signal at frequency 3f numerically and internal to the noise reduction system. This permits the determination of amplitude $a_1$ without affecting the noise at frequency 3f. Noise reduction reference signal generator 19 also generates a noise reduction signal of frequency 4.5f and coefficient calculator 20 determines filter coefficients appropriate to provide a noise reduction signal to drive the amplitude $a_2$ toward zero. However, in this example, it was desired that the amplitude at frequency 4.5f to be reduced to no less than 0.5 $a_2$. Since it is known that $a_2=0.6\ a_1$, the alternate leakage factor is applied by the leakage adjuster 18 when the noise at frequency 4.5f approaches $(0.5)(0.6)a_1$ or $0.3a_1$. Similarly, the alternate leakage factor is applied by leakage adjuster 18 when the noise at frequency 6f approaches $(0.4)(0.5)a_1$ or $0.2a_1$. Thus, the active noise reduction system can achieve the desired spectral profile in terms of amplitude $a_1$.

Numerous uses of and departures from the specific apparatus and techniques disclosed herein may be made without departing from the inventive concepts. Consequently, the invention is to be construed as embracing each and every novel feature and novel combination of features disclosed herein and limited only by the spirit and scope of the appended claims.

What is claimed is:

1. A method for operating an active noise reduction system in a vehicle comprising:

receiving a low latency signal representative of engine speed from a vehicle data bus;

transmitting a high latency signal representative of engine speed based on said low latency signal on a separate data bus;

processing the high latency signal to provide a noise reduction reference signal at a reference frequency, the reference frequency related to the engine speed;

determining whether an audio signal input from an audio source fulfils a triggering condition;

setting a leakage factor depending on the triggering condition; and processing the noise reduction reference signal using the leakage factor to generate a noise reduction audio signal at a frequency corresponding to a predetermined multiple of the reference frequency.

2. The method of claim 1, further comprising: transducing acoustic energy in an enclosed space to provide a noise signal representative of the noise in the enclosed space, and modifying, responsive to the noise signal, a phase and a magnitude of the noise reduction reference signal to generate the noise reduction audio signal.

3. The method of claim 2, wherein the determining the phase and magnitude of the noise reduction signal is performed by circuitry comprising an adaptive filter.

4. The method of claim 3, wherein the enclosed space is a vehicle cabin.

5. A method in accordance with claim 1, wherein said separate data bus is an entertainment bus or an entertainment control bus.

6. An assembly adapted to be used in a vehicle, comprising a vehicle data bus; a separate data bus; and an active noise reduction system comprising:

an element for receiving a low latency signal representative of engine speed from said vehicle data bus and for transmitting a high latency signal representative of engine speed based on said low latency signal on said separate data bus;

a noise reduction reference signal generator for processing the high latency signal to provide a noise reduction reference signal at a reference frequency, the reference frequency related to the engine speed;

a leakage adjuster for determining whether an audio signal input from an audio source fulfils a triggering condition and setting a leakage factor depending on the triggering condition; and noise reduction circuitry for processing the noise reduction reference signal using the leakage factor to generate a noise reduction audio signal at a frequency corresponding to a predetermined multiple of the reference frequency.

7. The assembly of claim 6, further comprising: a microphone for transducing acoustic energy in an enclosed space to provide a noise signal representative of noise in the enclosed space, wherein the noise reduction circuitry determines a phase and a magnitude of the noise reduction signal to generate the noise reduction audio signal.

8. The assembly of claim 6, wherein the noise reduction circuitry comprises an adaptive filter.

9. The assembly of claim 7, wherein the enclosed space is a vehicle cabin.

10. The assembly of claim 6, wherein said separate data bus is an entertainment bus or an entertainment control bus.

* * * * *